United States Patent
Catchmark et al.

(10) Patent No.: US 12,263,254 B2
(45) Date of Patent: *Apr. 1, 2025

(54) COMPOSITE MATERIALS

(71) Applicant: The Penn State Research Foundation, University Park, PA (US)

(72) Inventors: Jeffrey M. Catchmark, State College, PA (US); Yuzhi Deng, University Park, PA (US)

(73) Assignee: The Penn State Research Foundation, University Park, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/110,262

(22) Filed: Feb. 15, 2023

(65) Prior Publication Data

US 2023/0302189 A1    Sep. 28, 2023

Related U.S. Application Data

(63) Continuation of application No. 15/484,329, filed on Apr. 11, 2017, now Pat. No. 11,590,253, which is a continuation of application No. 14/198,415, filed on Mar. 5, 2014, now abandoned.

(60) Provisional application No. 61/772,716, filed on Mar. 5, 2013.

(51) Int. Cl.
| | |
|---|---|
| *A61L 15/28* | (2006.01) |
| *A61L 15/42* | (2006.01) |
| *B29C 44/34* | (2006.01) |
| *B29C 48/00* | (2019.01) |
| *B29K 401/00* | (2006.01) |
| *B29L 31/00* | (2006.01) |
| *C08J 9/00* | (2006.01) |
| *C08L 3/02* | (2006.01) |
| *C08L 5/08* | (2006.01) |

(52) U.S. Cl.
CPC ............. *A61L 15/28* (2013.01); *A61L 15/425* (2013.01); *B29C 44/3415* (2013.01); *B29C 48/022* (2019.02); *C08J 9/0061* (2013.01); *C08L 3/02* (2013.01); *C08L 5/08* (2013.01); *B29K 2003/00* (2013.01); *B29K 2401/00* (2013.01); *B29L 2031/753* (2013.01); *C08J 2207/10* (2013.01); *C08J 2303/02* (2013.01); *C08J 2405/08* (2013.01); *C08L 2203/02* (2013.01); *C08L 2203/14* (2013.01)

(58) Field of Classification Search
CPC ..... A61L 15/28; A61L 15/425; B29C 48/022; C08J 9/0061; C08L 3/02
See application file for complete search history.

(56) References Cited

U.S. PATENT DOCUMENTS

| | | | |
|---|---|---|---|
| 5,104,487 | A | 4/1992 | Taggart et al. |
| 5,256,711 | A | 10/1993 | Tokiwa et al. |
| 5,329,555 | A | 7/1994 | Marko et al. |
| 5,958,589 | A | 9/1999 | Glenn et al. |
| 6,329,565 | B1 | 12/2001 | Dutkiewicz et al. |
| 6,500,463 | B1 | 12/2002 | van Lengerich |
| 7,985,742 | B2 | 7/2011 | Bergeron |
| 8,975,387 | B1 | 3/2015 | Venditti et al. |
| 11,590,253 | B2 | 2/2023 | Catchmark et al. |
| 2001/0014388 | A1 | 8/2001 | Bastioli et al. |
| 2003/0049480 | A1 | 3/2003 | Gagliardini et al. |
| 2010/0189843 | A1 | 7/2010 | Xie et al. |
| 2011/0150972 | A1 | 6/2011 | Strickler et al. |
| 2013/0330417 | A1 | 12/2013 | Dong et al. |
| 2014/0256925 | A1 | 9/2014 | Catchmark et al. |
| 2017/0216477 | A1 | 8/2017 | Catchmark et al. |

FOREIGN PATENT DOCUMENTS

| | | |
|---|---|---|
| CA | 2308537 | 11/2000 |
| CA | 2426478 | 10/2003 |
| CA | 2483049 | 3/2005 |
| DE | 19729305 | 1/1999 |
| DE | 102006051560 | 5/2008 |
| JP | 2000-226401 | 8/2000 |
| KR | 2005-048579 | 5/2005 |
| WO | WO 2006/029519 | 3/2006 |

OTHER PUBLICATIONS

Nakamatsu, J. et al (Processing and characterization of porous structures . . . Biomacromol., vol. 7, pp. 3345-3355. (Year: 2006).*
Ortega-Ojeda, F. et al "Gel formation in mixtures of high amylopectin . . . " Carbohyd. Polym., vol. 56, pp. 505-514. (Year: 2004).*
Cinelli, P. et al."Foamed articles based on potato starch . . . " Polym. Degrad. Stabil., vol. 91, pp. 1147-1155. (Year: 2006).*
Kaisangsri, N. et al."Biodegradable foam tray from cassava starch . . . " Ind. Crops Prod., vol. 37, pp. 542-546. (Year: 2012).*
Srithongkham, S. et al."Starch/cellulose biocomposities . . . " vol. 2, No. 4, pp. 213-222. (Year: 2012).*
European Office Action in European Application No. 14760576.0 dated Jun. 28, 2019, 5 pages.
European Office Action in European Application No. 14760576.0 Dec. 8, 2017 3 pages.
Extended European Search Report issued in Application No. 14760576.0 dated Mar. 30, 2017, 2 pages.
Gimeno et al., "Effect of Xantham Gum and CMC on the Structure and Texture of Corn Flour Pellets Expanded by Microwave Heating," Cereal Chemistry, Jan. 2004, 81(1):100-107.
International Search Report and Written Opinion issued in International Application No. PCT/US2014/020751 mailed Jun. 26, 2014, 11 pages.
Onusseit, "Starch in industrial adhesives: new developments", Industrial Crops and Products, Dec. 1992, 1(2-4):141-146.

(Continued)

*Primary Examiner* — Leigh C Maier
(74) *Attorney, Agent, or Firm* — Fish & Richardson P.C.

(57) ABSTRACT

A composite material is formed by combining an expandable polymer having a charge with another polymer having an opposite charge to produce. In particular, the composite material can be prepared by combining the polymers with a medium such as and water, and expanding the mixture using a treatment that expands the mixture to produce, for example, insoluble porous foam-like composite

14 Claims, 2 Drawing Sheets

(56) References Cited

OTHER PUBLICATIONS

PCT International Preliminary Report on Patentability in International Appln. No. PCT US/2014/020751, dated Sep. 8, 2015, 7 pages.
Salam et al., "Synthesis and characterization of starch citrate—chitosan foam with superior water and saline absorbance properties," Biomacromolecules, May 2010, 11(6):1453-1459.
Stevens et al., "Starch-lingin foams", Express Polymer Letters, Apr. 2010, 4(5):311-320.
Tester et al., "Starch—composition, fine structure and architecture," J. Cereal Sci., Mar. 2004, 39(2):151-165.
The entire file history to corresponding U.S. Appl. No. 14/198,415, including U.S. PTO Office Action issued Jul. 6, 2017, 10 pages.
Waigh et al., "The phase transformations in starch during gelatinisation: a liquid crystalline approach," Carbohydrate Research, Sep. 2000, 328(2):165-176.
Wing, "Starch Citrate: Preparation and Ion Exchange Properties," Starch-Stärke, 1996, 48(7-8):275-279.
Written Opinion of the International Search Authority dated Sep. 17, 2015 issued in International Patent Application No. PCT/US2014/020751.
Xu et al., "Chitosan—starch composite film: preparation and characterization," Industrial Crops and Products, Mar. 2005, 21(2):185-192.

\* cited by examiner

COMPOSITE MATERIALS

CROSS-REFERENCE TO RELATED APPLICATION

This application is a continuation of U.S. patent application Ser. No. 15/484,329, filed Apr. 11, 2017, which in turn is a continuation of U.S. patent application Ser. No. 14/198,415, filed Mar. 5, 2014, which claims the benefit of U.S. Provisional Application Ser. No. 61/772,716, filed Mar. 5, 2013, the entire disclosure of each of these is hereby incorporated by reference herein.

STATEMENT REGARDING FEDERALLY SPONSORED RESEARCH

This invention was made with government support under Hatch Act Project No. PEN04436, awarded by the United States Department of Agriculture. The Government has certain rights in the invention.

TECHNICAL FIELD

The present disclosure relates to an insoluble porous foam-like composite material which can be formed by combining an expandable hydrophilic polymer with an oppositely charged hydrophilic polymer. In particular, the composite material can be prepared by combining the polymers with a polar medium, such as water, and expanding the mixture using a thermal treatment.

BACKGROUND

Insoluble low density, porous materials such as foams are needed for a wide variety of commercial applications including insulation materials, packaging materials, absorbent materials for applications ranging from personal hygiene to liquid hazardous waste remediation or removal, porous materials for biomedical applications including wound care and tissue regeneration, and, if edible, materials for food production such as 'puffed' food products or diet food products. Furthermore, materials which are compostable offer improved sustainability as they can be disposed safely in land fills or even used as an energy source through processes such as anaerobic digestion.

Starch, a natural biopolymer found in plants such as corn or potato, has been extensively utilized to develop expandable or so-called 'puffed' materials with other ingredients. Glenn et al. (U.S. Pat. No. 5,958,589, 1995) developed a starch-based microcellular foam using a novel solvent exchange method, and they claimed that such a material had superior properties such as improved mechanical strength, high pore volume, and low density. A starch-lignin foam was prepared by Stevens et al. (Stevens, E. S., Klamczynski, A., and Glenn, G. M. 2010. Starch-lignin Foams. Express Polymer Letters 4 (5): 311-320), which showed that a 20% replacement of starch with lignin had no adverse effect on foam density and morphology. More recently, Dougherty et al. (U.S. patent application #2010/0189843, 2010) described a hydroxypropylated starch to improve the extrusion process of a food composite whereby the hydroxypropylated starch aids in the retention of dietary fiber contained in the composite. Also, other biopolymers such as carboxymethyl cellulose and xanthum gum have been applied to expand with starch, which is said to improve the shape, texture and structure of starch-based composite. See Gimeno, E., Moraru, C. I., and Kokini, J. L. 2004. Effect of Xanthan Gum and CMC on the Structure and Texture of Corn Flour Pellets Expanded by Microwave Heating. Cereal Chemistry 81 (1): 100-107. Starch has also been used as an adhesive for the production of corrugated cardboard. See Onusseit, H. 1992. Starch in industrial adhesives: new developments. Industrial Crops and Products. 1(2-4):141-146. Starch composites which consist of principally biologically derived polymers, however, are typically soluble in polar solutions, limiting their use in many applications. Thus, a need exists to create insoluble composites such as insoluble starch composite with high liquid absorbing capability.

SUMMARY OF THE DISCLOSURE

An advantage of the present invention is a composite material that can be used for a variety of applications. Advantageously, the composite is insoluble in liquid environments and capable of absorbing many times its own weight. The composite can also be used as an adhesive.

These and other advantages are satisfied, at least in part, by a composite material such as a foam-like porous material composition which is insoluble in liquid environments. Advantageously the composite material is capable of absorbing many times it s own weight, e.g., as much as about 11 times its weight, in liquid and over a wide pH range, e.g., a pH range of about 2-12.

Embodiments of the present invention include an insoluble low density porous composite material containing at least one polymer having a charge, e.g., an anionic starch, and at least one polymer of opposite charge, e.g., cationic polysaccharide such as chitosan.

Another aspect of the present disclosure includes a process of preparing a composite material. The process comprises mixing at least one soluble polymer having a charge, e.g., at least one anionic polymer, at least one soluble polymer of opposite charge, e.g., at least one cationic polymer, and at least one polar solvent, e.g., water. Advantageously, at least one of the soluble polymers in the mixture is capable of expanding. The mixture is then expanded by one or more techniques that are known to expand at least one expandable polymer. Such techniques include, for example, thermal treatment, e.g., such as where the temperature of the treatment exceeds about 100 degrees Celsius, thermal extrusion, a microwave treatment, etc.

Additional embodiments include wherein the anionic starch is not gelatinized, the anionic starch contains at least 75% w/w amylopectin, the anionic starch is in an amount of at least 75% w/w and the oppositely charged polymer, e.g., a cationic polysaccharide, is between 2% w/w and 10% w/w, the polar solvent or the water is in an amount between 40% w/w and 80% w/w water in the mixture. The composites can also advantageously include other additives such as between 1% w/w and 25% w/w cellulose or nanocellulose, between 0.01% w/w to 1% w/w polyhexamethylene biguanid, antimicrobial agents, such as between 1% and 5% of sodium benzoate, etc. The present disclosure also contemplates the composites made by the processes described herein.

Additional advantages of the present invention will become readily apparent to those skilled in this art from the following detailed description, wherein only the preferred embodiment of the invention is shown and described, simply by way of illustration of the best mode contemplated of carrying out the invention. As will be realized, the invention is capable of other and different embodiments, and its several details are capable of modifications in various obvious respects, all without departing from the invention.

Accordingly, the drawings and description are to be regarded as illustrative in nature, and not as restrictive.

BRIEF DESCRIPTION OF THE DRAWINGS

FIG. 1(a) shows the swelling ratio with a pH 2, FIG. 1(b) shows the swelling ratio with a pH 7 and FIG. 1(c) shows the swelling ratio with a pH 12.

DETAILED DESCRIPTION OF THE DISCLOSURE

Figure 1:
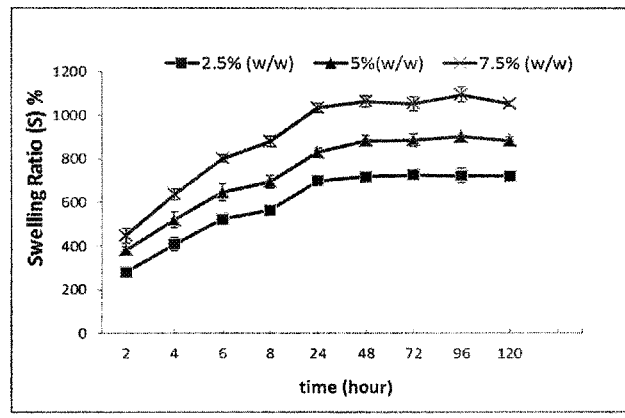
FIGS. 1(a)-1(c) provide three graphs showing the determination of swelling ratio (water uptake in % w/w of water to dry composite) of starch-chitosan composites swollen in solutions with different pH values according to embodiments of the present disclosure.
Figure 1:
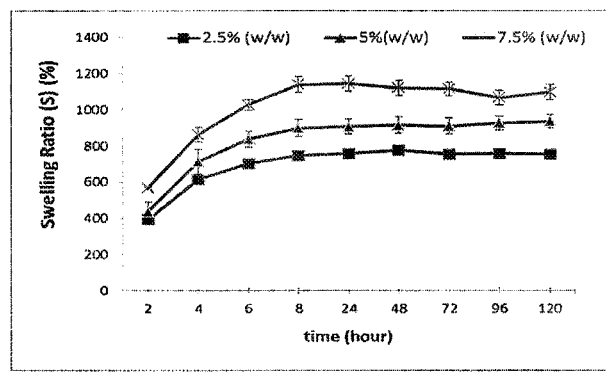
Figure 1:
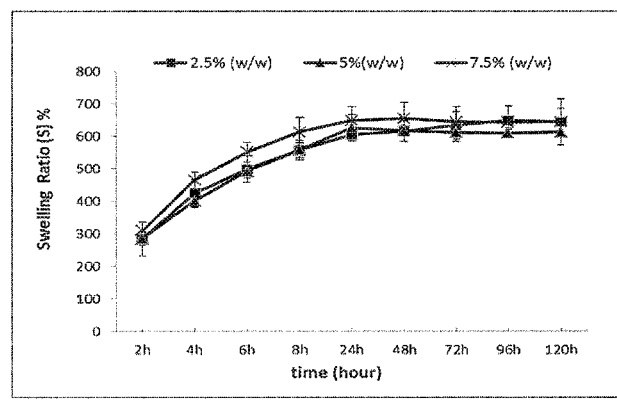

The present disclosure relates to composite materials that are insoluble in liquid environments but can absorb a large amount of liquid. The composite materials of the present disclosure can advantageously absorb a liquid in an amount that is many times its own weight, e.g., as much as about 11 times its weight, and over a wide pH range, e.g., a pH range of about 2-12. Other advantages of the composites of the present disclosure include a very simple production process. In addition some of the composites can be fabricated to yield completely compostable materials when produced using natural biologically derived polymers. The composites can also be formed or molded into a wide variety of shapes, including a process where the hydrated material is dehydrated within a mold where it can expand during dehydration to fill the mold and take the shape of the mold. In an aspect of the present disclosure, the mold would have some pores to allow water vapor to escape. Composites of the present disclosure include, for example, insoluble low density composites such as highly porous foams containing at least one polymer having a charge, e.g., an anionic starch, and at least one polymer of opposite charge, e.g., cationic polysaccharide such as chitosan.

The composites can be prepared by mixing at least one soluble polymer having a charge, at least one soluble polymer of opposite charge, and at least one polar solvent, wherein at least one of the soluble polymers is capable of expanding. The mixture is then expanded.

Soluble polymers useful for the present disclosure include, for example, polymers that are soluble in the polar solvent and carrying either a negative or positive charge. Such polymers having a charge include anionic polymers, such as, for example, at least one anionic starch, alginic acid, pectin, xanthan gum, hyaluronic acid, chondroitin sulfate, keratin sulfate, gum arabic, gum karaya, gum tragacanth, heparin, chondroitin, polyacrylic acid and it's derivatives, many proteins such as the caseins.

Soluble polymers of opposite charge, e.g., cationic polymers, that are soluble in the polar solvent include, for example, at least one cationic polysaccharide such as chitosan, cationic guar gum, cationic hydroxyethylcellulose, cationic starch, cationic cellulose, pectin, and cationic polyethylene glycol.

Polar solvents useful for solubilizing the polymers include, for example, water, aqueous solvents including ethylene or propylene glycol, alkyl lactate, and optionally alcohol or organic carbonates, lower alcohols such as methanol, ethanol, n-propanol and isopropanol.

It is believed that the polymers while soluble in the polar solvent when forming the mixture become insoluble upon expansion because the cationic polymer electrostatically crosslinks with the anionic polymer during the expansion process where the polymers can interact.

In one aspect of the present disclosure, the process of preparing the composite material includes preparing a mixture containing (i) at least one anionic starch as the at least one soluble polymer having a charge, (ii) at least one cationic polysaccharide as the at least one soluble polymer of opposite charge, and (iii) at least one polar solvent, e.g. water. The mixture is then expanded by one ore more techniques that are known to expand the at least one expandable polymers. Such techniques include, for example, thermal treatment, e.g., such as where the temperature of the treatment exceeds about 100 degrees Celsius, thermal extrusion, a microwave treatment, etc. Starch, for example, especially amylopectin, is well known to exhibit extensive expansion capacity under thermal processing, including microwave heating and thermal extrusion. Expanded starch, however, is readily soluble in aqueous solutions.

An expandable soluble polymer such as an anionic starch can be combined with a cationic polymer such as chitosan and water to expand the mixture through microwave processing or other thermal treatments such as thermal extrusion. The anionic starch can be an anionic amylopectin or a starch which contains phosphate such as many starches derived from potato (where the starch contains one phosphate ester group per approximately 40 to 400 anhydroglucose units). The cationic polymer can also be a cationic guar or cationic starch.

It is preferable to use a starch which has not been gelatinized to improve the characteristics of the expanded composite including the degree of expansion during thermal treatment which would result in a lower density insoluble composite.

For example, an expanded insoluble composite can be produced using the following process. Chitosan solution was prepared by mixing chitosan (Sigma-Aldrich, Saint Louis, MO) in 1% (v/v) formic acid and magnetically stirred at 600 rpm for 24 hours under room temperature. The pH of the chitosan solutions ranged from 4 to 5; the preferred pH is 4.5. The contents of chitosan in the above solutions ranged from 1.67% to 5% (w/v), preferably at about 5% (w/v). After the chitosan was dissolved and the solution became clear, the solution was poured into a container for further mixing with potato starch (MP Biomedicals, Solon, Ohio).

Starch-based chitosan composite foams were prepared as follows. 2.7 ml chitosan solutions with different concentrations ranged from 1.67% to 5% (w/v) were added to 1.8 gram non-gelatinized potato starch powder (containing at least 50-75% amylopectin). The final weight ratios of chitosan to potato starch were from 2.5% to 7.5% (w/w), where ratio of 7.5% was most desired. The starch-chitosan mixtures were then stirred at 250 rpm for about 2 minutes. After blending, the mixtures were heated by microwave at 100% power of 900 W at 2450 MHz for 35-50 seconds.

FIGS. 1(a)-1(c) show the swelling ratio (water uptake in % w/w of water to dry composite) of varied starch-chitosan composites prepared by microwave treatment. Swelling behavior was examined at three different pH values: 2, 7 and 12. It is shown in FIGS. 1(a)-1(c) that all composites can be immersed in acidic (pH2), neutral (pH7) and basic (pH12) environment and remain insoluble for as long as 120 hours. The swelling equilibriums for different starch composites are different depending on specific pH environment. Specifically, composites immersed in pH 2 and pH 12 reached equilibrium faster than that at pH 7. At pH 2 and pH 12, the equilibrium was achieved after immersion for 8 hours, whereas at pH 7 it took 24 hours to achieve equilibrium.

Generally speaking, the higher the chitosan content in the composite, the better the swelling ratio will be in solution, except the case at pH12. At pH 2, the maximum values of swelling ratio for 2.5%, 5% and 7.5% starch-chitosan composite were 746%, 896% and 1137%, respectively. Likewise, at pH7 the maximum swelling ratios for 2.5%, 5% and 7.5% starch-chitosan composite were 698%, 896% and 1035%, respectively. However, such a behavior did not exist at pH12 where swelling ratios for all composites showed no significant difference, and the maximum swelling ratio reached around 613% for all composites after equilibrium. Furthermore, composites immersed in lower pH behave better than those immersed in higher pH in terms of swelling ratio. Take 7.5% starch-chitosan composite, for example, the maximum swelling ratios at pH2, pH7 and pH12 were 1137%, 1035% and 613%, respectively. Such a performance can be seen in 2.5% and 5% starch-chitosan composites as well.

Other additives can also be included in the composite. For example, cellulose or other insoluble polymer fiber can be added to modify the mechanical properties of the composites. Specifically, starch:chitosan:cellulose composites can be created with modified properties where the component ratios can range from approximately 50-80% starch, 2-10% chitosan, and 10-48% cellulose. To reduce brittleness, approximately 1% to 25% of glycerol can be added w/w relative to the total dry weight of all composite components. Glycerol can be added and mixed into the solution before microwave, thermal extrusion, or other thermal processing. Other additives are also possible including but not limited to polyethylene glycol, poly lactic acid, or poly lactic glycolic acid. Final hydration levels before thermal processing can range from approximately 40% to 80% where 60% is preferred. Other component additives may be more suitable for specific applications. For example, collagen may provide a benefit for biomedical applications. In addition, various additives such as antimicrobial and therapeutic agents can be added before or after microwave processing. Therapeutic agents include compounds such as polyhexamethylene biguanide (PHMB), sodium benzoate, or any contained in U.S. Patent Application 20110150972, 2011. If added as a solution after microwave processing by soaking the composite in solution or spraying a solution onto the composite, the composite can be subsequently dehydrated by freeze drying to permit long term storage. The use of chitosan in the composite may provide some measure of natural antimicrobial properties.

Insoluble expanded or non-expanded starch composites as described above using other production techniques can also be employed to prepare the composite. These production techniques include various extrusion, molding and electrospinning techniques, both of which are well known to those skilled in the art. Electrospinning of starch based materials is well known and often involves solvents other than water such as, for example, ethanol. The use of other polar solvents other than water is acceptable in the formation of any of the composites described herein.

As disclosed herein, improvements to extruded and electrospun material can be achieved by adding cellulose and glycerol. In the case of materials with dimensions less than 1 mm, nanocellulose, cellulose nanofibers, cellulose nanocrystals or cellulose nanowhiskers can be used as the cellulose material. These forms of cellulose are cellulose materials which exhibit at least one dimension less than about 100 nm.

EXAMPLES

The following examples are intended to further illustrate certain preferred embodiments of the invention and are not limiting in nature. Those skilled in the art will recognize, or be able to ascertain, using no more than routine experimentation, numerous equivalents to the specific substances and procedures described herein.

Starch-chitosan composite foams were prepared as follows. Chitosan solutions were prepared with different concentrations ranging from 1.67% to 5% (w/v) by mixing chitosan (available from Sigma Aldrich, Saint Louis, MO) having a molecular weight between approximately 2 kDa and 100 kDa, where higher molecular weights may be preferred, including those in excess of 100 kDa, in an acidic solution where formic acid was added to DI water to a pH between 4 and 5, preferably 4.5 where the final concentration of chitosan ranged from approximately 1.67% to 5% (w/v), preferably at about 5% (w/v). Then 2.7 ml of the chitosan solution was added to 1.8 grams of non-gelatinized potato starch powder (containing at least 50-75% amylopectin) (available from MP Biomedicals, Solon, Ohio). The final weight ratios of chitosan to potato starch were from 2.5% to 7.5% (w/w). A final weight ratio of chitosan to potato starch of 7.5% was most desired to produce a composite which exhibited the most water absorption capacity and which was the most stable when submerged for prolonged periods (approximately 5 days) in highly acidic (pH 2) or highly basic (pH 12) solutions. The starch-chitosan mixtures were then stirred at 250 rpm for about 2 minutes. After blending, the mixtures were heated by microwave at 100% power of 900 W at 2450 MHz for 35-50 seconds. During the microwave treatment water is converted to water vapor and the starch gelatinizes in the presence of the chitosan. The generation of water vapor causes the viscous starch-chitosan mixture to expand until dehydrated. During this process, the cationic chitosan binds with the anionic starch creating an insoluble composite.

While the claimed invention has been described in detail and with reference to specific embodiments thereof, it will be apparent to one of ordinary skill in the art that various changes and modifications can be made to the claimed invention without departing from the spirit and scope thereof. Thus, for example, those skilled in the art will recognize, or be able to ascertain, using no more than routine experimentation, numerous equivalents to the specific substances and procedures described herein. Such equivalents are considered to be within the scope of this invention, and are covered by the following claims.

What is claimed is:

1. An expanded insoluble composite material comprising:
   at least 75% w/w of at least one gelatinized anionic starch;
   between 2% w/w and 10% w/w of at least one cationic polysaccharide, wherein the cationic polysaccharide is chitosan;
   between 1% w/w and 25% w/w cellulose or nanocellulose; and
   an electrostatic crosslink disposed between said at least one gelatinized anionic starch and said at least one cationic polysaccharide, wherein the composite material is insoluble in a polar solvent, and wherein the at least one gelatinized anionic starch was gelatinized from non-gelatinized anionic starch in the presence of the at least one cationic polysaccharide to form the composite material.

2. The composite material of claim 1, wherein the composite material is insoluble in water.

3. The composite material of claim 1, wherein the composite material is a porous foam.

4. The composite material of claim 1, wherein the gelatinized anionic starch comprises at least 75% w/w amylopectin.

5. The composite material of claim 1, wherein the composite material comprises between 1% w/w and 25% w/w cellulose.

6. The composite material of claim 1, wherein the composite material comprises between 1% w/w and 25% w/w nanocellulose.

7. The composite material of claim 1, wherein the composite material is characterized by a swelling ratio of greater than 200% at a pH of 2 for water uptake in % w/w of water to a dry form of the composite material.

8. A wound care product comprising the expanded insoluble composite material of claim 1.

9. An insulating product comprising the expanded insoluble composite material of claim 1.

10. An expanded insoluble composite material prepared from a mixture comprising:
    (i) at least one non-gelatinized anionic starch;
    (ii) at least one cationic polysaccharide, wherein the cationic polysaccharide is chitosan;
    (iii) at least one polar solvent; and
    (iv) cellulose or nanocellulose; and,
    wherein in a single step, the mixture is expanded while removing the at least one polar solvent while gelatinizing said at least one non-gelatinized starch in the presence of the at least one polysaccharide of opposite charge to form the composite material including gelatinized starch and said at least one polysaccharide, wherein the composite material is insoluble in a polar solvent, and
    wherein the composite material comprises:
        at least 75% w/w of the at least one gelatinized anionic starch;
        between 2% w/w and 10% w/w of the at least one cationic polysaccharide; and
        between 1% w/w and 25% w/w of the cellulose or nanocellulose.

11. The composite material of claim 10, wherein the composite material is a porous foam that is insoluble in the at least one polar solvent.

12. The composite material of claim 10, wherein the composite material is insoluble in water.

13. The composite material of claim 1, further comprising between 1% w/w and 25% w/w glycerol.

14. An expanded insoluble composite material comprising:
    50-80% w/w of at least one gelatinized anionic starch;
    2-10% w/w of chitosan; and
    10-48% w/w cellulose; and
    an electrostatic crosslink disposed between said at least one gelatinized anionic starch and said chitosan, wherein the composite material is insoluble in a polar solvent, and wherein the at least one gelatinized anionic starch was gelatinized from non-gelatinized anionic starch in the presence of the chitosan to form the composite material.

* * * * *

UNITED STATES PATENT AND TRADEMARK OFFICE
CERTIFICATE OF CORRECTION

PATENT NO.       : 12,263,254 B2
APPLICATION NO.  : 18/110262
DATED            : April 1, 2025
INVENTOR(S)      : Jeffrey M. Catchmark and Yuzhi Deng It is certified that error appears in the above-identified patent and that said Letters Patent is hereby corrected as shown below:

On the Title Page

Column 2, (Other Publications), Line 1: please delete "(Processing" and insert therefor -- "Processing --;

Column 2, (Other Publications), Line 2: before "Biomacromol.," – please insert -- " --;

Column 2, (Other Publications), Line 9: please delete "biocomposities" and insert therefor -- biocomposites --;

Column 2, (Other Publications), Line 17: please delete "Xantham" and insert therefor -- Xanthan --; and Column 2, (57) Abstract, Line 7, After "composite" please insert -- . --.

Signed and Sealed this
Eighteenth Day of November, 2025

John A. Squires
*Director of the United States Patent and Trademark Office*